United States Patent [19]

Nakao et al.

[11] 4,339,345

[45] Jul. 13, 1982

[54] METHOD FOR MANUFACTURE OF NICKEL BORIDE COLLOID

[75] Inventors: Yukimichi Nakao, Tokyo; Shoei Fujishige, Yokohama, both of Japan

[73] Assignees: Agency of Industrial Science & Technology; Ministry of International Trade & Industry, both of Tokyo, Japan

[21] Appl. No.: 160,921

[22] Filed: Jun. 19, 1980

[30] Foreign Application Priority Data

Jul. 3, 1979 [JP] Japan .................................. 54-84726

[51] Int. Cl.$^3$ ...................... B01J 13/00; C07C 29/136
[52] U.S. Cl. .................... 252/309; 252/432; 568/881
[58] Field of Search .............................. 252/432, 309

[56] References Cited

PUBLICATIONS

Paul et al., Industrial & Engineering Chemistry, vol. 44, No. 5, pp. 1006–1010, 1952.
Nakao et al., Chemistry Letters, Chemical Society of Japan, pp. 995–996, 1979.
Brown et al., J.A.C.S., 85, p. 1005, 1963.

*Primary Examiner*—G. T. Breitenstein
*Attorney, Agent, or Firm*—Oblon, Fisher, Spivak, McClelland & Maier

[57] ABSTRACT

Nickel boride colloid useful as a catalyst for the hydrogenation of carbonyl compound is obtained by causing a nickel salt to react upon an alkali metal borohydride in an alcohol substantially free from dissolved oxygen under a non-oxidative atmosphere in the presence of an alcohol-soluble polymer.

6 Claims, No Drawings

METHOD FOR MANUFACTURE OF NICKEL BORIDE COLLOID

BACKGROUND OF THE INVENTION

This invention relates to a method for the manufacture of nickel boride colloid which possesses a remarkably high catalytic activity in the hydrogenation of carbonyl compounds.

Heretofore, nickel boride has been used such as in the form of a fine powder which is obtained by the reaction of sodium borohydride upon a nickel salt solution (Ind. Eng. Chem., 44, 1006 (1952)) or in the form of a homogeneous colloidal solution which is obtained by the reaction of sodium borohydride upon a nickel salt in an alcohol solvent in the presence of a suitable polymer (Chemistry Letters, 995 (1979)). It has been known to exhibit a high catalytic activity comparable to the activity of Raney nickel in the hydrogenation of a carbon-carbon double bond.

These forms of nickel boride which have heretofore been used exhibit a decidedly lower catalytic activity in the hydrogenation of unsaturated bonds other than the carbon-carbon double bond, such as, for example, the carbon-oxygen double bond. Under the conditions of normal room temperature and atmospheric pressure, they produce substantially no catalysis in the hydrogenation. The hydrogenation of a compound possessing a carbon-oxygen double bond, namely, a carbonyl compound, for the production of a corresponding alcohol is a reaction of great industrial significance. This reaction generally relies upon Raney nickel catalyst. Nevertheless this catalyst entails rigid conditions of elevated temperatures and high pressure for effective performance.

SUMMARY OF THE INVENTION

The inventors devoted a diligent study to developing a method for the manufacture of a nickel boride having a higher catalytic activity in the hydrogenation of carbonyl compounds than the conventional catalysts. Their study has led to a discovery that a clear nickel boride colloid possessing a remarkably high catalytic activity in the hydrogenation of carbonyl compounds is obtained by causing a nickel salt to react upon an alkali metal borohydride in an alcohol in the presence of an alcohol-soluble polymer intended as a protective colloid and subsequently adding a basic substance to the resultant reaction mixture, or by causing a nickel salt to react upon an alkali metal borohydride in an alcohol containing an insoluble basic substance in the presence of an alcohol-soluble polymer. The present invention has issued from this knowledge.

An object of this invention is to provide a method for the manufacture of a catalyst highly useful for the hydrogenation of carbonyl compounds under conditions of normal room temperature and atmospheric pressure.

DESCRIPTION OF THE PREFERRED EMBODIMENT

According to this invention, a nickel boride colloid having a notably high catalytic activity in the hydrogenation of carbonyl compounds is produced by causing a nickel salt to react upon an alkali metal borohydride in an alcohol in the presence of an alcohol-soluble polymer intended as a protective colloid and subsequently adding a basic substance to the resultant reaction mixture, or by causing a nickel salt to react upon an alkali metal borohydride in an alcohol containing an insoluble basic substance in the present of an alcohol-soluble polymer.

The nickel salt to be used as one of the raw materials for the product of this invention is required to be soluble in alcohols. Preferred examples of salts which satisfy the requirement are sulfates and hydrochlorides.

Examples of alcohols which are preferably used as the solvent are lower alcohols of one to three carbon atoms, i.e., methanol, ethanol, 1-propanol and 2-propanol which are capable of dissolving alkali metal borohydrides.

Examples of alcohol-soluble polymers which serve advantageously as the protective colloid include poly(vinylpyrrolidone), poly(methyl vinyl ether), poly(2-hydroxyethyl acrylate), poly(tert-butyl methacrylate) and soluble nylon.

Examples of alkali metal borohydrides which are used advantageously herein include sodium borohydride and potassium borohydride. The alkali metal borohydride is desired to be used in an amount of at least 1.5 mols per mol of the nickel salt. The upper limit set to this amount of the alkali metal borohydride is 5 mols. If the amount of the alkali metal borohydride falls short of the lower limit of 1.5 mols mentioned above, the catalytic activity of the produced nickel boride colloid is low. If this amount exceeds the upper limit, however, the excess alkali borohydride is decomposed to produce a large amount of sodium borate, which is liable to upset the stability of colloidal dispersion and induce precipitation of colloidal particles.

For this invention, the presence of a basic substance in the reaction system constitutes an essential requirement. This presence of the basic substance in the reaction system may occur after the reaction of the nickel salt upon the alkali metal borohydride. When the basic substance is of a kind insoluble in alcohols, the basic substance may be added to the alcohol solution before the addition thereto of the alkali metal borohydride. When the reaction for the production of the colloid of this invention is allowed to proceed in the absence of the basic substance, the product to be obtained exhibits a very poor catalytic activity in the hydrogenation of carbonyl compounds. Examples of basic substances which are usable herein for the purpose described above include alcoholates and hydroxides of alkali metals such as alcohol-soluble sodium alcoholate, potassium alcoholate, sodium hydroxide and potassium hydroxide, quaternary ammonium hydroxides such as tetrabutylammonium hydroxide, and alcohol-insoluble solid basic substances such as potassium carbonate.

The amount in which the basic substance is added is from the lower limit of 2 mols to the upper limit of 10 mols per mol of the nickel salt where the basic substance is soluble in alcohols. This amount is desired to be not less than 10 mols and not more than 1000 mols per mol of the nickel salt where the basic substance is a solid insoluble in alcohols. If the amount of the basic substance to be added falls short of the lower limit mentioned above, the produced nickel boride colloid exhibits a notably lower catalytic activity in the hydrogenation of carbonyl compound than is expected. If this amount exceeds the upper limit, however, the excess alkali metal ions present in the reaction system are liable to impair the stability of colloidal dispersion and induce precipitation of colloidal particles.

The reaction by the method of this invention must be carried out in the absence of oxygen. If the reaction proceeds in the presence of oxygen, the nickel boride formed in the system is rapidly decomposed, the reaction solution is discolored to light brown and the product is deprived of its catalytic activity. For the method of this invention to be advantageously effected, the nickel salt and the alcohol-soluble polymer prescribed above are dissolved in an alcohol which has been deoxygenated in advance under a non-oxidative atmosphere such as, the atmosphere of hydrogen, nitrogen, argon or helium.

The amounts of the nickel salt and alcohol-soluble polymer to be dissolved in the alcohol are desired to fall in the respective ranges of 0.1 to 10 g and 0.1 to 10 g per 1000 cc of the alcohol. If the amount of the nickel salt thus added falls short of the lower limit, the oxygen contained in a minute amount in the alcohol decomposes the formed nickel boride colloid to an extent of conspicuously lowering the catalytic activity of the colloid. If this amount exceeds the upper limit, the colloidal dispersion tends to become instable and induce precipitation. If the amount of the alcohol-soluble polymer to be added falls short of the lower limit, the colloidal dispersion tends to become instable and induce precipitation. If this amount exceeds the upper limit, however, the produced nickel boride colloidal solution acquires added viscosity and loses its catalytic activity.

The next step of the method of the invention is to stir the resultant solution at temperatures in the range of from 0° to the boiling point of the alcohol to be used, preferably from 10° to 30° C., and add dropwise the solution of the alkali metal borohydride in an alcohol into the former solution being stirred as described above. Subsequently, the resultant mixture is stirred with the basic substance added thereto in the form of an alcohol solution or in a solid form. When the basic substance to be used is an insoluble solid, its addition is effected prior to the dropwise addition of the alcohol solution of the alkali metal borohydride; in other words, the presence of the basic substance in the reaction system may occur either during or before the dissolution of the nickel salt and the alcohol-soluble polymer.

Consequently, there is obtained a homogeneous blackish brown nickel boride colloid. When the basic substance to be used is an alcohol-insoluble solid, the solid basic substance remains in its undissolved state in the resultant reaction solution. In this case, a similarly homogeneous nickel boride colloid can be obtained by allowing the reaction solution to stand until the solid basic substance sediments to the bottom and thereafter separating the supernatant from the solution. The presence in the solution of the solid basic substance in its undissolved state, however, has no adverse effect on the catalytic activity of the colloid.

The primary characteristic of the homogeneous nickel boride colloid which is obtained by the present invention resides in the notably high catalytic activity to be exhibited in the hydrogenation of carbonyl compounds. Use of this colloid as a catalyst enables the hydrogenation of various aldehydes and ketones to proceed rapidly under the mild conditions of normal room temperature and atmospheric pressure and give rise to corresponding primary and secondary alcohols. The second characteristic of the colloid is that particles of nickel boride contained in the colloid are remarkably fine. Owing to this fineness of the particle, even compounds of the kind which have bulky substituents disposed about carbonyl groups (namely, the compounds of the general formula,

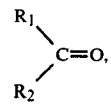

wherein $R_1$ and $R_2$ each denote a phenyl group or some other similar group) and which are not easily hydrogenated by use of an ordinary catalyst of an nonuniform particle size can be advantageously hydrogenated by use of this colloid as the catalyst. The third characteristic of the colloid consists in the use of the alcohol as the dispersion medium. Consequently, a varying carbonyl compound can be smoothly dissolved in the colloid and the hydrogenation of this carbonyl compound can be effected in a homogeneous liquid phase.

The high catalytic activity which the nickel boride colloid obtained by this invention exhibits in the hydrogenation of carbonyl compounds is fully manifested on condition that the nickel boride forms a homogeneous colloidal state and the colloid is used in the presence of a basic substance. Use of a mixture of finely divided particles of nickel boride with a base brings about no catalytic activity in the hydrogenation of a carbonylic compound. If the nickel boride colloid is used without incorporation of the base, the catalytic activity to be exhibited is less than 1/20 of the activity obtained with the colloid incorporating the base.

Now, the invention will be described more specifically with reference to working examples.

EXAMPLE 1

A flask having an inner volume of 50 ml was charged with 23.8 mg of nickel chloride (II) ($NiCl_2.6H_2O$) and 10 mg of poly(vinylpyrrolidone) (with a polymerization degree 360) and the air trapped within the flask was displaced with hydrogen. Thereafter, 14 ml of ethanol was added to dissolve the compounds in the flask. The resultant solution was stirred under the conditions of 30° C. of temperature and one atmosphere of hydrogen gas and 5 ml of an ethanol solution containing 7.56 mg of sodium borohydride was added dropwise to the stirred solution. This addition causes sudden change of the color of the solution to dark blackish brown. To this solution, 1 ml of an ethanol solution containing 16.0 mg of sodium hydroxide was further added dropwise. Consequently, there was obtained nickel boride colloid (having a nickel content of 0.29 mg/cc). When 18.4 $\mu$l of acetone was added to this nickel boride colloid (20 ml), hydrogenation of acetone immediately ensued to produce 18.7 $\mu$l of 2-propanol (0.25 m.mol). This hydrogenation was accompanied by absorption of hydrogen. This absorption of hydrogen proceeded at an initial velocity of 7.1 $H_2$ m.mol/Ni mol.sec and terminated in about 15 minutes. When the procedure described above was repeated without the addition of sodium hydroxide, the nickel boride colloid finally obtained exhibited a very low catalytic activity in the hydrogenation of acetone. In the absorption of hydrogen involved in this case was 0.3 $H_2$ m.mol/Ni mol.sec. The nickel boride colloid which was produced in the presence of sodium hydroxide exhibited a catalytic activity in the hydrogenation of methyl isobutyl ketone (31.3 $\mu$l), acetophenone (29.4 $\mu$l), benzophenone (45.5 mg, added as contained in 1 ml of ethanol solution), benzaldehyde (25.2

μl) and butyl aldehyde (22.4 μl) under the conditions of 30° C. and one atmosphere, with the absorption of hydrogen ensuing at respective initial velocities of 5.2, 5.9, 5.2, 12.6 and 9.5 $H_2$ m.mol/Ni mol.sec, to produce corresponding alcohols. All the portions of ethanol used herein were invariably refluxed in advance under the atmosphere of argon to be freed from dissolved oxygen.

EXAMPLE 2

The procedure of Example 1 was followed, except 10 mg of soluble nylon (a product of Toray composed of 6:66:610 at a proportion of 3:4:3) was used in the place of poly(vinylpyrrolidone). Consequently, there was obtained homogeneous blackish brown nickel boride colloid. With this colloid as a catalyst, 18.4 μl of acetone was hydrogenated under the conditions of 30° C. and one atmosphere, with the absorption of hydrogen ensuing at an initial velocity of 2.8 $H_2$ m.mol/Ni mol.sec. The absorption of hydrogen terminated in about 45 minutes. This hydrogenation produced 18.7 μl of propanol.

EXAMPLE 3

A flask having an inner volume of 50 ml was charged with 23.8 mg of nickel chloride (II), 10 mg of poly(vinylpyrrolidone) and 276 mg of anhydrous potassium carbonate, and the air entrapped within the flask was displaced with hydrogen. Thereafter, 15 ml of ethanol freed in advance from dissolved oxygen was added to the flask to dissolve the nickel chloride (II) and poly(vinylpyrrolidone). At the end of this dissolution, the anhydrous potassium carbonate remained therein in its undissolved stage. The resulaant solution was kept stirred under the conditions of 30° C. and one atmosphere of hydrogen, and 5 ml of ethanol solution containing 7.56 mg of sodium borohydride was added dropwise to the stirred solution. Consequently, the solution suddenly changed color to blackish brown. The solution containing the undissolved anhydrous potassium carbonate was stirred for two hours and then left to stand until the solids sedimented to the bottom. Then, the nickel boride colloid aimed at was obtained in the form of supernatant. This colloid was transferred into a separate flask having an inner volume of 50 ml and having the entrapped air displaced in advance with hydrogen. When 18.4 μl of acetone was poured into the colloid under the conditions of 30° C. and one atmosphere, absorption of hydrogen ensued at an initial velocity of 8.1 $H_2$ m.mol/Ni mol.sec to produce 2-propanol. This absorption of hydrogen terminated in about 20 minutes. The hydrogenation produced 18.7 μl of 2-propanol. When acetone was poured into the colloid which contained the undissolved solids of anhydrous potassium carbonate, absorption of hydrogen ensued at an initial velocity of 8.1 $H_2$ m.mol/Ni mol.sec, a value precisely equal to the initial velocity of hydrogen absorption obtained by use of the colloid freed in advance from the solids. The duration of hydrogen absorption and the amount of produced 2-propanol were also identical.

EXAMPLE 4

The procedure of Example 1 was repeated, except methanol was used in the place of ethanol. Consequently, there was obtained a homogeneous blackish brown nickel boride colloid. With this colloid as the catalyst, 18.4 μl of acetone was hydrogenated, with the absorption of hydrogen ensuing at an initial velocity of 3.1 $H_2$ m.mol/Ni mol.sec. The absorption of hydrogen terminated in about 60 minutes.

EXAMPLE 5

The procedure of Example 1 was followed, except 26.8 mg of sodium ethoxide and 103.6 mg of tetra-n-butylammonium hydroxide were used each as the additive base in the place of sodium hydroxide. In each run, there was obtained a uniform blackish brown nickel boride colloid. With the colloids as the catalyst, 18.4 μl of acetone was hydrogenated under the conditions of 30° C. and one atmosphere, with the absorption of hydrogen ensuing at respective initial velocities of 7.0 and 5.0 $H_2$ m.mol/Ni mol.sec. The absorption of hydrogen terminated within 15 minutes and 25 minutes respectively.

What is claimed is:

1. A method for the manufacture of nickel boride colloid, which method comprises causing a nickel salt to react upon one member selected from the group consisting of sodium borohydride and potassium borohydride in an alcohol substantially free from dissolved oxygen under a non-oxidative atmosphere in the presence of one member selected from the group consisting of poly(vinylpyrrolidone), poly(methyl vinyl ether), poly(2-hydroxyethyl acrylate, poly(tertbutyl methacrylate) and soluble nylon, and subsequently adding one member selected from the group consisting of soduim alcoholate, potassium alcoholate, sodium hydroxide, potassium hydroxide, tetrabutylammonium hydroxide and potassium carbonate to the resultant reaction mixture.

2. The method according to claim 1, wherein the nickel salt is one member selected from the group consisting of sulfates and hydrochlorides.

3. The method according to claim 1, wherein the alcohol is one member selected from the group consisting of methanol, ethanol, 1-propanol and 2-propanol.

4. A method for the manufacture of nickel boride colloid, which method comprises causing a nickel salt to react upon one member selected from the group consisting of sodium borohydride and potassium borohydride in an alcohol containing potassium carbonate and containing substantially no dissolved oxygen under a non-oxidative atmosphere in the presence of one member selected from the group consisting of poly(vinylpyrrolidone), poly(methyl vinyl ether), poly(2-hydroxyethyl acrylate, poly(tertbutyl methacrylate) and soluble nylon.

5. The method according to claim 4, wherein the nickel salt is one member selected from the group consisting of sulfates and hydrochlorides.

6. The method according to claim 4, wherein the alcohol is one member selected from the group consisting of methanol, ethanol, 1-propanol and 2-propanol.

* * * * *